US00RE36080E

United States Patent [19]

Perrine

[11] E Patent Number: Re. 36,080

[45] **Reissued Date of Patent: *Feb. 2, 1999**

[54] METHOD FOR AUGMENTING FETAL HEMOGLOBIN

[75] Inventor: Susan P. Perrine, Richmond, Calif.

[73] Assignee: Children's Hospital Medical Center of Northern California, Oakland, Calif.

[ * ] Notice: The portion of the term of this patent subsequent to Apr. 18, 2006, has been disclaimed.

[21] Appl. No.: 79,325

[22] Filed: Jun. 18, 1993

Related U.S. Patent Documents

Reissue of:

[64] Patent No.: 5,025,029
Issued: Jun. 18, 1991
Appl. No.: 518,454
Filed: May 4, 1990

U.S. Applications:

[63] Continuation-in-part of Ser. No. 277,151, Nov. 29, 1988, abandoned, which is a continuation-in-part of Ser. No. 917,805, Oct. 10, 1986, Pat. No. 4,822,821.

[51] Int. Cl.[6] ..... A61K 31/19; A61K 31/195; A61K 31/16

[52] U.S. Cl. ..... 514/557; 514/561; 514/629; 514/815

[58] Field of Search ..... 514/381, 517, 514/557, 561, 578, 815, 629

[56] References Cited

U.S. PATENT DOCUMENTS

| | | | |
|---|---|---|---|
| 4,482,571 | 11/1984 | Abraham | 424/317 |
| 4,731,381 | 3/1988 | Abraham et al. | 514/571 |
| 4,822,821 | 4/1989 | Perrine | 514/557 |

OTHER PUBLICATIONS

Constantoulakis P. et al., 1988. "Alpha–amino–n–butyric Acid Stimulates Fetal Hemoglobin in the Adult". Blood 72: 1961–67.

Daniel P., et al., 1989. "Pharmacokinetic Study of Butyric Acid In Vivo as Sodium and Arginine Butyrate Salts". Clin.Chim. Acta 181: 255–263.

Karlsson, S. and Nienhuis, A.E., 1985. "Developmental Regulation of Human Globin Genes". Annu.Rev.Biochem. 54: 1071–1108.

Miller, A.A. et al., 1987. "Clinical Pharmacology of Sodium Butyrate Ion in Patients with Acute Leukemia". Eur.J.Cancer Clin. Oncol. 23: 1283–1287.

Murata et al., 1988. "EDF Initiates the Terminal Differentiation of Friend Leukemia Cells, Inducing de novo Hemoglobin Synthesis ". J. Ferbnt. Technol. 66(5): 501–507.

Noguchi et al., 1988. "Levels of Fetal Hemoglobin Necessary for Treatment of Sickle Cell Disease". N.Eng.J.Med. 318: 96–99.

Perrine, S.P. et al., 1989. "Butyrate Analogs Modulate Globin Gene Expression in Human and Ovine Erythroid Cells". Prog.Clin.Biol.Res 1989, 316B pp. 341–350.

Perrine, S.P. et al., 1989. "Butyric Acid Modulates Developmental Globin Gene Switching in Man and Sheep". Adv.Exp.Med.Biol. 271: 177–183.

Perrine, S.P. et al., Jul. 1989. "Sodium Butyrate Enhances Fetal Globin Gene Expression in Erythroid Progenitors of Patients with Hb SS and Beta–Thalassemia", Blood 74(1): 454–459.

Perrine, S.P. et al., Nov. 1988. "Butyrate Infusions in the Ovine Fetus Delay the Biological Clock for Globin Gene Switching", Proc.Natl.Acad.Sci.USA 85:8540–8542.

Perrine, S.P. et al., 1987. "Inhibition of Fetal Globin Gene Swtiching In Vivo in Human and Ovine Fetuses", Alan R. Liss, Inc.: Developmental Control of Globin Gene Expression 545–554.

Perrine, S.P. et al., 1987. "Butryric Acid Analogs Augment Gamma–Globin Gene Expression in in Neonatal Erythroid Progenitors", Biochem. Biophys. Res. Commun. 148(2): 694–700.

Perrine, S.P. et al., 1985. "Delay in the Fetal Globin Switch in Infants of Diabetic Mothers". N. Engl.J.Med. 312: 334–338.

Schechter, A.N. and C.T. Noguchi, 1979. "Inhibition of Sickle Hemoglobin Gelation by Peptides". In: Development of Therapeutic Agents for Sickle Cell Disease, eds. J. Rosa, Y. Beuzard and J. hercules, North–Holland Publishing Company, Amsterdam–New York–Oxford.

Tsuji et al., 1988. Structural and Biological Identity of Recombinant EDF (Erythroid Differentiation Factor) with Natural EDF. Agric. Biol. Chem. 52(9): 2143–2148.

Wood, W.G. et al., 1980. HbF Synthesis in Sickle Cell Anemia: A Comparison of Saudi Arab Cases with Those of African Origin. Br.J.Haematol. 45: 432–445.

S.P. Perrine et al., "Control of the Fetal Globin Switch In Vitro", *J. Cell. Biochem.*, Supp. 10D, 1986, p. 40 (1986).

S.P. Perrine et al., "Investigation of Developmental Globin Gene Switching In Infants Of Diabetic Mothers", in *Molecular Approaches To Developmental Biology*, R.A. Firtel and E.H. DAvidson Eds., pp. 501–508 (1987).

S.P. Perrine et al., "Butyric Acid Modulates Developmental Globin Gene Switching In Man And Sheep", in *Molecular Biology of Erythropoiesis* J.L. Ascensao et al. Ed., pp. 177–183 (Jun. 1989).

*Primary Examiner*—Phyllis G. Spivack
*Attorney, Agent, or Firm*—James F. Haley, Jr.; Margaret A. Pierri; Fish & Neave

[57] ABSTRACT

A method is provided for inhibiting the γ to β-globin switching in subjects afflicted with β-globin disorders. The method is particularly adapted for ameliorating the clinical symptoms of sickle cell anemia by periodically introducing butyrate, α-*amino-n-butyric acid,* or [certain isomers, homologs, analogs or chemical variations thereof.] *isobutyramide* into the bloodstream of the subject prior to natural completion of the switching process.

4 Claims, No Drawings

METHOD FOR AUGMENTING FETAL HEMOGLOBIN

Matter enclosed in heavy brackets [ ] appears in the original patent but forms no part of this reissue specification; matter printed in italics indicates the additions made by reissue.

This *application is a Reissue of Ser. No. 07/518,454, filed May 5, 1990, U.S. Pat. No. 5,025,029, which* is a continuation-in-part of copending Ser. No. 277,151, filed Nov. 29, 1988, now abandoned which is a continuation-in-part of Ser. No. 917,805, filed Oct. 10, 1986, now U.S. Pat. No. 4,822,821.

*This invention was made with government support under HL-37118 awarded by the National Institutes of Health. The government has certain rights in the invention.*

The present invention is directed to a method for inhibiting or reversing the switching in in vivo or in vitro from production of γ to β-globin, thus augmenting the production of fetal hemoglobin. In particular, the present invention is directed to a method for controlling the fetal hemoglobin switch by introducing into the bloodstream of the fetus or child or into erythroid cultures a compound of the formula I, described hereinbelow.

BACKGROUND OF THE INVENTION

Normal adult hemoglobin comprises four globin proteins, two of which are α proteins and two of which are β proteins. Diseases known as sickle cell syndromes are associated with disorders in the β chain of the hemoglobin. However, in mammals, and particularly in humans, during fetal development, the fetus produces a fetal hemoglobin which comprises, instead of β-globin proteins, two γ-globin proteins. At some point during fetal development or infancy, depending on the particular species and individual, there is a so-called globin switch wherein the erythrocytes in the fetus switch from making predominantly γ-globin to making predominantly β-globin. It has been observed, however, that increased levels of fetal hemoglobin (derived from γ-globin) ameliorate the severity of sickling disorders. It has also been observed that subjects heterozygous for hereditary persistence of fetal hemoglobin syndromes (HPFH) and sickling hemoglobin (HbS) are clinically asymptomatic of sickle cell anemia. Also, infants with sickle cell anemia do not usually develop the symptoms of the disease until approximately four months of age when their fetal hemoglobin levels decrease. These observations suggest that a method for increasing the levels of fetal hemoglobin would be beneficial to patients with sickle cell syndromes.

It is thus an object of the present invention to provide a method for inhibiting or reversing the γ to β-globin switch in a fetus or infant to maintain increased fetal hemoglobin levels in those individuals with sickle cell syndromes.

Since inhibition of the γ to β-globin gene switch has been observed in infants of diabetic mothers (IDM), it appears that disturbances in normal metabolites in the bloodstream might disrupt a normally timed and fixed gene-switch. Two metabolites, insulin and butyric acid, have been observed as being elevated in infants of diabetic mothers. Some investigators have shown that factors in serum can effect the γ to β-globin switching, particularly around the time the switch occurs. There has been, however, heretofore no development of a non-toxic therapeutic method or natural agent to increase fetal hemoglobin in subjects with sickle cell disease.

It is thus another object of the present invention to provide an agent for maintaining a high level of γ chain synthesis (thereby maintaining high fetal hemoglobin levels), without toxicity and long term side effects, by using a physiologic factor rather than a chemotherapeutic agent.

SUMMARY OF THE INVENTION

The present invention provides a method for ameliorating β-globin disorders in mammals comprising the step of periodically introducing into the bloodstream of said mammal during its gestation period and/or early infancy and thereafter, an amount of a compound of the formula I:

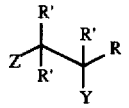

I wherein R is —*CONH*$_2$, —$CO_2R_1$, —$SO_2R_1$, —$SO_3R_1$, or

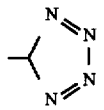

and $R_1$ is [$NH_2$,] H, M, branched or linear alkyl 1–4 carbons or partially or perfluorinated branched or linear alkyl of 1–4 carbon atoms, and M is a cation; Z is —$CH_3$, —X, or —$CX_3$; and X is H, Cl, F, Br, I or combinations thereof; Y is H, —$NH_2$, —$NH_3^+$, —$CX_3$ or F; and R' is H or F; or mixtures of these, sufficient to inhibit or reverse fetal γ to β-globin switching. The method according to the present invention is particularly useful for ameliorating in humans the clinical effects of sickle cell anemia.

DESCRIPTION OF THE INVENTION

The present invention provides a method for ameliorating the clinical effects of β-globin disorders, particularly the disorder of sickle cell anemia and β-thalassemias. The present invention is advantageous in that the compounds utilized are physiologic factors, i.e., natural metabolites found in the bloodstream of mammals and are thus, when introduced into the bloodstream, not likely to have toxic or undesirable long term side effects.

In accordance with the present invention, a compound of the formula I or a mixture of two or more thereof, are introduced into the bloodstream of the subject shown to or suspected of having a β-globin disorder, such as sickle cell anemia or β-thalassemias. The foregoing may be administered as their non-toxic salts, such as their sodium salts, ammonium salts, potassium salts, and the like. Preferred compounds are L-β-amino-n-butyric acid, L-α-amino-n-butyric acid, DL-α-amino-n-butyric acid, sodium butyrate, β-chloro-D-alanine, 3-chloro-[proprionic]*propionic* acid, 5-(2-chloroethyl)tetrazole, heptafluoro-butyric acid, α-amino propane sulfonic acid, and sodium propanesulfinate, isobutyramide, perfluoroisobutyric acid, arginine, heptafluorobutyric acid, isobutyric acid, similar fluorinated or branched chain analogs, and particularly arginine salts.

Methods used to introduce the compound will be any convenient method normally used to introduce pharmaceuticals into the bloodstream, such as by injection or infusion, catheter, syringe, transcutaneous patch, in-dwelling depot delivery systems, and the like. Oral or parenteral administration may also be utilized.

The exact size of an effective does of a compound according to the method of the present invention will depend on a number of factors including the particular recipient and the severity of condition, thus the route of administration will be ultimately at the discretion of the attendant physician.

While it is possible to utilize the compounds in vivo as a raw chemical, it is preferable to present them as a pharmaceutical formulation. The formulation of the present invention comprises a compound as previously described together with one or more acceptable carriers therefor and, optionally other therapeutic ingredients. The carriers must be acceptable in the sense of being compatible with other ingredients of the formulation and not dilatory as to the recipient.

For oral administration, the formulations may be presented as discrete units such as capsules, or tablets each containing a predetermined amount of the active ingredient, as a powder or granules, as a solution or suspension in an aqueous or nonaqueous liquid, as an oil in water liquid emulsion or as a water in oil liquid emulsion.

Formulations for parenteral administration include aqueous or nonaqueous sterile injection solutions which may contain antioxidants, buffers, bacteriostats and solutes which render the formulation isotonic with the blood of the intended recipient. The formulation may be presented in dose unit or multi-dose containers such as ampules or vials and may be stored in a freeze-dried condition requiring only the addition of a sterile liquid carrier, for example water, for injections.

Preferred unit dosage formulations are those containing a daily dose or a unit daily subdose, or an appropriate fraction thereof.

As further application of the compounds according to the present method, they may be utilized in vitro to cell cultures taken from patients to determine the potential efficacy of further treatment for the β-globin disorders, such as sickle cell anemia. The compounds may be thus used in vitro in cell cultures from patients to determine whether further addition of one of the compounds would result in continued inhibition or reversal of the globin switch.

The frequency and dosages of administration of the above compounds will depend upon when the compound is introduced, whether the subject is a fetus or an infant, the size and weight of the subject, the condition of the pregnant mother, and the like. Generally, injections beginning at a dosage as low as about 12 mg/kg body weight per day during gestation, particularly prior to the thirty-second week of gestation in humans, will delay the γ to β switching. Typically, larger dosages in the range of 500–1000 mg/kg of estimated fetal weight will be useful. Higher dosages may be utilized at the discretion of the physician. Since apparently the switching process is not complete in humans until approximately four months after birth, treatment may be preferentially initiated after birth up until about the fourth month of infancy and continued as long as necessary to maintain enhanced fetal hemoglobin levels in the patient. However, initiation of treatment even subsequent to the fourth month may also be effective.

All treatment should preferably occur prior to the fourth month of infancy since the γ to β switching process is difficult to reverse. Although treatment with one of the above compounds prior to the fourth month of infancy will inhibit the γ to β-switching process, treatment subsequent to that period may also achieve the desired clinical results, i.e., the amelioration of the effects of the β-globin disorder. Therefore, if the switching process is inhibited even to the extent of 10 to 20% (that is, the subject makes 10 to 20% more γ-globin than would be expected if the switch were allowed to occur), this may be sufficient to ameliorate the symptoms of the disease.

The method according to the present invention may be utilized in vivo, or in vitro as a diagnostic test. For the in vitro test erythroid cultures, such as that obtained from cord blood mononuclear cells in Iscove's Modified Dulbecco's Medium with 0.9% methylcellulose, may be used as described by Stamatoyannopoulous et al., Blood 54, 440–450 (1979) and Friedman et al., J. Clin. Invest., 75, 1359–1368 (1985). The cultures may be formed with and without the addition of various metabolites whose concentrations are observed to increase in infants of diabetic mothers (IDM). To show the effect of such factors, insulin (0.1–100 ng/ml), Insulin Growth Factor I (4–10 ng/ml), Isoleucine (4–10 mcg/ml), and butyric acid (0.01–10 mM) were added to the cultures. Some cultures were performed in 95% nitrogen to simulate a hypoxic intrauterine environment, and IDM plasma was used instead of fetal calf serum in some cultures. Colonies were harvested and incubated with $^3$H-leucine under the same culture conditions for the last 24 hours. Globin production was analyzed by electrophoresis on Triton-urea gels, autoradiography, and densitometry and by radioligand immunoassay of the total and fetal hemoglobin in pg per Bfu-e-derived cell was performed as described in Stamatoyannopoulous et al. and Friedman et al., ibid. In 10 Cfu-e (culony-forming unit-erythroid) cultures from five normal infants and five term IDM mean β-globin synthesis (expressed as percent of total non-α synthesis), was 42.3% β-globin and 17.3% respectively. This is equivalent to the β-globin levels produced in infants' reticulocytes. This difference in percent β-globin synthesis between the IDM and normal infant Cfu-e was ($p<0.001$, Student's t-test) and indicates that these relatively late erythroid progenitors are committed to a pattern of globin production in the fetal environment. The percentage of β-globin synthesized by Bfu-e (burst-forming unit-erythroid) from normal term infants did not differ statistically from the percentage produced by their Cfu-e. However, Bfu-e from IDM produced a significantly higher percentage of the β-globin than did the infants Cfu-e and reticulocytes ($p<0.05$). This difference indicates that switching to increased β-globin production occurred once the more primitive progenitors were removed from the abnormal intrauterine environment or that the process began in vivo. Thus, the apparent in vitro switching by Bfu-e cultures from premature infants of less than 33 weeks gestation and from term IDM (pre-switch infants) is an assay system for testing the effect on globin switching of physiological parameters peculiar to the diabetic intrauterine environment, in which the globin switch is delayed. The addition of insulin, IGF-I, isoleucine, or low oxygen conditions cause the Bfu-e to synthesize the equivalent or more β-globin than control cultures.

Sodium butyrate (at 0.1 mM concentrations), caused Bfu-e from pre-switch infants to synthesize significantly less β-globin than did Bfu-e in control cultures. This affect of sodium butyrate was not found consistently in infants in whom the switch had occurred before birth, however, increased γ-globin synthesis was found consistently with α-amino-n-butyric acid. A significant increase in accumulation of hemoglobin F in the cord blood erythroid colonies also occurred in nine out of eleven cultures from seven infants, grown in the presence of sodium-butyrate compared to control cultures ($p<0.05$). This effect on increasing hemoglobin F in culture was not due to toxicity since the pH of the culture media was not effected, and similar numbers of Bfu-e and Cfu-e were not found in cultures grown in the presence or absence of the butyrates. Radioimmunoassay of Bfu-e hemoglobin indicates complete hemoglobinization (>15 pg/cell) in the presence of butyrate, demonstrating that the observed increase in hemoglobin F synthesis and accumulation were not an artifact of retardation of globin production.

The following examples are provided by way of illustration, however, the invention is not intended to be limited in any manner thereby.

EXAMPLE 1

Cultures of erythroid progenitors from blood obtained during the first three years of life of Hb SS (sickle cell syndrome) infants are tested. It is found that DL-α, L-α or L-β butyric acid or their sodium salts, or β-Cl-D-alanine, 3-[CL-proprionic]*Cl-propionic* acid, 5-(2-chloroethyl) tetrazole, heptafluoro-butyric acid, α-aminopropane sulfonic acid, or sodium propane sulfinate, increase β-globin synthesis in two-thirds of infant cord blood erythroid colonies, SS samples from infants, even when the infants' reticulocytes and control colonies (Bfu-e) synthesize nearly all β-globin.

EXAMPLE 2

In peripheral blood erythroid cultures established from infant sickle cell anemia patients it was found that butyrate enhances γ globin synthesis by approximately 14% compared to control cultures from the same patients. This would achieve corresponding Hb F synthetic levels of greater than 20% in most patients.

EXAMPLE 3

A Dexter culture is established from cord blood from an infant with sickle cell anemia whose mother has diabetes. This infant was prenatally diagnosed and has almost no $\beta^S$ globin on electrophoresis. Progenitors assayed weekly for globin synthesis from this infant's erythroid progenitors cultured in the presence and absence of α-amino-n-butyric acid and insulin showed that the combination of these two agents prevented switching at two weeks. Her control cells switched from 9% $\beta^S$ globin to 20%. The treated cells still synthesize only 9% $\beta^S$ globin.

EXAMPLE 4

Four fetal sheep were treated with continuous infusions of butyrate in utero and the fetal to adult (β) hemoglobin switching process was delayed in three of the four. In one, the "switch" was completely inhibited. This lamb had 100% fetal globin at birth, a time when controls produce 80–100% adult globin. When the infusion was begun in this lamb, β (adult) globin was only 4%. In two of the lambs, the switch was delayed; these two lambs already produced approximately 15% adult globin when the infusion was started; they produced half of that found in controls at birth. In the fourth fetal lamb in whom adult β-globin production was already 35% when the infusion started, a response was not found, implying that early treatment may be of primary importance in inhibiting the process.

EXAMPLE 5

Erythroid cultures (progenitors) from twelve sickle cell anemia patients of various ages were cultured for 14 days in presence of 0.1 mM sodium butyrate, and the total hemoglobin and fetal hemoglobin were assayed. The results are shown below in Table 1. In all cases the percent fetal hemoglobin produced was greater in the treated cultures than in untreated controls.

TABLE 1

Radio-Ligand Assay of Hemoglobin Produced by Erythroid Progenitors

| Patient | Total Hb, pg per cell | HbF, pg per cell | Percent HbF |
|---|---|---|---|
| 1. Control | 32.6 | 4.0 | 12.3 |
| Butyrate | 32.5 | 7.1 | 21.8 |
| 2. Control | 16.2 | 1.8 | 11.1 |
| Butyrate | 15.9 | 3.7 | 23.3 |
| 3. Control | 29.3 | 1.8 | 6.3 |
| Butyrate | 24.5 | 3.05 | 12.4 |
| 4. Control | 29.4 | 5.9 | 20.0 |
| Butyrate | 30.0 | 7.8 | 26.0 |
| 5. Control | 24.6 | 2.7 | 11.0 |
| Butyrate | 28.2 | 7.2 | 25.5 |
| 6. Control | 25.6 | 4.18 | 16.3 |
| Butyrate | 18.8 | 6.65 | 35.4 |
| 7. Control | 25.6 | 7.92 | 30.9 |
| Butyrate | 19.7 | 7.35 | 37.3 |
| 8. Control | 24.7 | 1.63 | 6.6 |
| Butyrate | 21.4 | 3.61 | 16.9 |
| 9. Control | 12.9 | 2.27 | 17.6 |
| Butyrate | 18.0 | 4.2 | 23.2 |
| 10. Control | 44.5 | 32.1 | 72.1 |
| Butyrate | 41.5 | 43.2 | 100.0 |
| 11. Control | 12.5 | 5.2 | 41.6 |
| Butyrate | 19.7 | 10.9 | 55.3 |
| 12. Control | 11.1 | 4.5 | 40.5 |
| Butyrate | 12.6 | 5.8 | 46.0 |
| 13. Control | | | 70.0 |
| L-alpha-amino-n-butyric acid | | | 80.0 |
| 14. Control | | | 50.0 |
| [Chloroproprionic] *Chloropropionic* Acid | | | 70.0 |
| 15. Control | | | 25.0 |
| [Isobutyramine] *Isobutyramide* | | | 38.0 |

EXAMPLE 6

Erythroid cultures from five β-thalassemia patients were cultured in the presence of sodium butyrate as described in Example 6 and the α/non-α globin ratios were assayed. The results are shown in Table 2. In all cases the butyrate lowered the ratio compared to control cultures, indicating a lowering of excess α-globin levels (which cause the damage by an increase in γ-globin). The lowering of the excess α-globin levels ameliorates, and in some instances may eliminate, the need for chronic transfusions.

TABLE 2

Alpha to Non-Alpha Globin Ratios

| Patient Phenotype | Control | Butyrate |
|---|---|---|
| 1. β° Thalassemia | 2.5 | 1.6 |
| 2. β° Thalassemia | 1.75 | 0.91 |
| 3. $B^+$ Thalassemia | 1.76 | 1.33 |
| 4. HbE-β° Thalassemia | 4.65 | 4.11 |
| 5. HbE-β° Thalassemia | 5.7 | 2.8 |

EXAMPLE 7

Three fetal sheep are treated with continuous infusions in utero as in Example 4, using heptafluorobutyric acid. In all three sheep, decrease in β-globin is observed within three days, thus evidencing a reversal of the switch. This effect persists for 5 days off treatment.

What is claimed is:

[1. A method for ameliorating β-globin disorders in a mammal comprising the step of introducing into the bloodstream of said mammal periodically during its gestation period and/or infancy, a compound of the formula I:

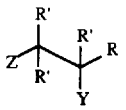

I wherein R is $—CO_2R_1$, $—SO_2R_1$, $—SO_3R_1$, or

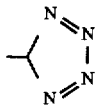

and $R_1$ is $NH_2$, H, M, branched or linear alkyl 1–4 carbons or partially or perfluorinated branched or linear alkyl of 1–4 carbon atoms, and M is a cation; Z is $—CH_3$, —X, or $—CX_3$; and X is H, Cl, F, Br, I or combinations thereof; Y is H, $—NH_2$, $—NH_3^+$, $—CX_3$ or F; and R' is H or F; or a mixture thereof, in an amount, frequency and duration of life sufficient to inhibit or reverse fetal γ to β-globin switching.]

[2. A method according to claim 1 wherein said mammal is human and said disorder is sickle cell anemia.]

[3. A method according to claim 1 wherein said mammal is human and said disorder is β-thalassemia.]

4. A method [according to claim 2 or 3 wherein said compound comprises] *for ameliorating sickle cell anemia or β-thalassemia in a human comprising the step of introducing into the bloodstream of said human periodically during its gestation period and/or infancy* α-amino-n-butyric acid *in an amount, frequency and duration of life sufficient to inhibit or reverse fetal γ to β-globin switching.*

5. A method [according to claim 2 or 3 wherein said compound comprises] *for ameliorating sickle cell anemia or β-thalassemia in a human comprising the step of introducing into the bloodstream of said human periodically during its gestation period and/or infancy* sodium butyrate *in an amount, frequency and duration of life sufficient to inhibit or reverse fetal γ to β-globin switching.*

[6. A method according to claim 2 or 3 wherein said compound comprises β-chloro-D-alanine.]

[7. A method according to claim 2 or 3 wherein said compound comprises 3-chloro-proprionic acid.]

[8. A method according to claim 2 or 3 wherein said compound comprises 5-(2-chloroethyl)tetrazole.]

[9. A method according to claim 2 or 3 wherein said compound comprises heptafluorobutyric acid.]

[10. A method according to claim 2 or 3 wherein said compound comprises α-aminopropanesulfonic acid.]

[11. A method according to claim 2 or 3 wherein said compound comprises sodium propanesulfinate.]

[12. A method according to claim 1 wherein said γ to β-globin switching is is inhibited to the extent that γ-globin synthesis in said mammal remains at 10 to 20% above normal levels after birth.]

[13. A method according to claim 2 or 3 wherein said compound comprises chloroproprionic acid.]

14. A method [according to claim 2 or 3 wherein said compound comprises] *for ameliorating sickle cell anemia or β-thalassemia in a human comprising the step of introducing into the bloodstream of said mammal periodically during its gestation period and/or infancy* isobutyramide *in an amount, frequency and duration of life sufficient to inhibit or reverse fetal γ to β-globin switching.*

*15. The method according to any one of claims 4, 5 or 14 wherein said γ- to β-globin switching is inhibited to the extent that γ-globin synthesis in said human remains at 10 to 20% above normal levels after birth.*

* * * * *